United States Patent [19]

DePrince

[11] Patent Number: 4,663,147

[45] Date of Patent: May 5, 1987

[54] DISC-LIKE SUSTAINED RELEASE FORMULATION

[75] Inventor: Randolph B. DePrince, Terre Haute, Ind.

[73] Assignee: International Minerals & Chemical Corp., Terre Haute, Ind.

[21] Appl. No.: 771,816

[22] Filed: Sep. 3, 1985

[51] Int. Cl.$^4$ .......................... A61K 9/44; A61K 9/28; A61K 9/30; A61K 9/32

[52] U.S. Cl. .................................... 424/467; 604/890; 604/891; 604/892; 424/473

[58] Field of Search ........................ 424/15, 32, 33, 94, 424/19-22; 604/890, 891, 892

[56] References Cited

U.S. PATENT DOCUMENTS

| | | | |
|---|---|---|---|
| 2,851,648 | 12/1974 | Brooke | 128/260 |
| 3,113,076 | 12/1963 | Jacobs | 424/15 |
| 3,146,169 | 8/1964 | Stephenson et al. | 424/15 |
| 3,993,072 | 11/1976 | Zaffaroni | 128/260 |
| 4,036,228 | 7/1977 | Theeuwes et al. | 128/260 |
| 4,052,505 | 10/1977 | Higuchi et al. | 424/14 |
| 4,164,560 | 8/1979 | Folkman et al. | 424/22 |
| 4,218,433 | 8/1980 | Kooichi | 424/15 |
| 4,278,087 | 7/1981 | Theeuwes et al. | 128/260 |
| 4,298,003 | 11/1981 | Theeuwes et al. | 128/260 |
| 4,357,312 | 11/1982 | Hsieh et al. | 424/15 |
| 4,391,797 | 7/1983 | Folkman et al. | 424/19 |
| 4,449,983 | 5/1984 | Cortese | 604/892 |
| 4,503,030 | 3/1985 | Edgren et al. | 424/15 |

FOREIGN PATENT DOCUMENTS 1372040 10/1974 United Kingdom .................. 424/15

*Primary Examiner*—Shep K. Rose
*Attorney, Agent, or Firm*—W. R. Guffey; T. L. Farquer

[57] ABSTRACT

A device for the release of a diffusible solid in a fluid medium which comprises a disc which comprises a substantially uniform mixture of said diffusible solid and a polymer which is insoluble in and impermeable to said fluid medium and impermeable to said diffusible solid. The surfaces of said disc are coated with a polymer which is insoluble in and impermeable to said fluid medium and impermeable to said diffusible solid, with the exception of one or more apertures which extend through the disc and expose a portion of the mixture of diffusible solid and polymer to the fluid medium when the device is immersed therein. The aperture or apertures are placed in said disc such that as said fluid medium enters the disc through said aperture or apertures, the ratio of surfce area of diffusible solid exposed to the fluid medium to the length of the path through which the exposed solid must diffuse to exit the disc remains substantially constant.

16 Claims, 5 Drawing Figures

DISC-LIKE SUSTAINED RELEASE FORMULATION

FIELD OF THE INVENTION

This invention relates to a sustained release device for the delivery of a beneficial agent to living beings. More specifically, this invention relates to such a delivery device which can be implanted, inserted into body cavities of living beings or orally ingested by living beings for the release of the beneficial agent, a diffusible solid, at a controlled and substantially steady rate for a prolonged period of time.

BACKGROUND OF THE INVENTION

In many therapeutic, medical and veterinary programs, it is desirable and necessary to provide for the slow release of a beneficial agent to a living being at a controlled rate over a prolonged period of time. In many cases, it is desirable that the rate of release of the agent be constant or have a zero order time dependence in order that the living being continuously receives a uniform amount of beneficial agent.

Different approaches have been tried to obtain a sustained-release device which would release a beneficial agent at a controlled rate. One method used is to mix the drug with a carrier material that is gradually broken down by body fluids, the drug being released as the carrier disintegrates. Waxes, oils, fats and soluble polymers are some materials that have been used as the carriers in these systems. Constant release or zero order release has not been obtained by this method since as the carrier disintegrates, the surface area of the dosage unit decreases, exposing smaller quantities of the carrier to the surrounding body fluids and thus decreasing the release rate of the medicament.

Another approach, set out in U.S. Pat. No. 3,113,076, is to design a solid tablet form with at least one aperture so that during disintegration of the tablet, the total area subject to disintegration and release of active medicament remains relatively constant. The constant release is obtained because the surface area available to release the medicament decreases on the outer surface as it disintegrates and increases on the inner surface as that surface disintegrates, keeping the total surface area available for release relatively constant. This type of disintegrating tablet, however, does not last for a prolonged period of time and is meant only for oral administration rather than for implantation or insertion into body cavities. In one embodiment, U.S. Pat. No. 3,113,076 provides for the outer surface of the tablet to be coated with an insoluble material so that the disintegration occurs only at the inner surface. This, however, eliminates the constant release advantage, for the rate of release of the medicament will increase as the inner surface area increases with the widening disintegration of the material from the center outward.

U.S. Pat. No. 3,851,648, issued to Brooke, discloses another approach to the zero-order release problem wherein the rate of release is achieved by the configuration of a cavity within a delivery device and a slot which connects the cavity and the exterior of the device. The configuration is such as to provide an increasing surface area of diffusible substance exposed to the fluid medium within the container as the length of the path through which the dissolved substance must diffuse to reach the exterior increases. The device of the invention, an implant, is cylindrical in shape with a rectangular slot lengthwise on one side which communicates with an internal cavity, the cross-section of which is shaped like a slice of pie. This implant is quite complicated to make and different medicaments will require different sized slots and cavities to retain the zero order release advantage. Thus, the device of this invention requires various manipulations and calculations before it can be prepared in the proper size and configuration to disperse a specific desired medicament at a substantially constant rate. The suggested material for the container is stainless steel, which may cause problems in fabricating the device to meet certain specifications and may cause a negative reaction when implanted into a living being.

U.S. Pat. No. 3,146,169, issued to Stephenson and Spence, represents an attempt to achieve constant rate release from a tablet composition by covering the medicament portion with an inert portion and having a hole through the inert portion into the medicament. This method is unsatisfactory in that it provides a reservoir system wherein the release rate will only be constant as long as the medicament portion stays saturated with the drug to be released. After the medicament portion is no longer saturated with the drug, the release rate will drop off rapidly. Thus, the order of release is controlled not by the type of device and the drug employed, but by the concentration of the drug inside and outside of the device.

The object of the invention is to provide a simple, easily manufactured device for the controlled, substantially constant release of beneficial agent.

A further object of the invention is to provide a device for the release of a beneficial agent in a living being wherein the release will continue for a prolonged period of time.

A still further object of the invention is to provide devices which can be conveniently produced for the release of a variety of beneficial agents.

A still further object of the invention is to provide a biocompatible device which can be implanted, inserted into a body cavity of a living being or orally ingested by a living being.

SUMMARY OF THE INVENTION

In accordance with the present invention, there is disclosed a device for the release of a diffusible solid in a fluid medium which comprises: a disc which comprises a substantially uniform mixture of the diffusible solid and a polymer which is insoluble in and impermeable to the fluid medium and impermeable to the diffusible solid, wherein the surfaces of the disc are coated with a polymer which is insoluble in and impermeable to the fluid medium and impermeable to the diffusible solid, with the exception that one or more apertures extend through the disc and expose a portion of the mixture of diffusible solid and polymer to the fluid medium when the device is immersed therein. The aperture or apertures are placed in the disc such that as the fluid medium enters the disc through the aperture or apertures the ratio of surface area of diffusible solid exposed to the fluid medium to the length of the path through which the exposed solid must diffuse to exit the disc remains substantially constant.

The device can be prepared by mixing the polymer and the diffusible solid, forming a cylindrical disc, coating the disc with a polymer and making one or more apertures in the center of the disc which extend through the disc and the polymeric coating.

The present invention also relates to a method of administering a diffusible solid to a living being by implantation of this device into body tissues, insertion of the device into a body cavity or oral ingestion by the living being.

BRIEF DISCRIPTION OF THE DRAWINGS

DETAILED DESCRIPTION OF THE INVENTION

A device for the release of a diffusible solid into a fluid medium at a substantially constant rate comprises a mixture of a diffusible solid and a polymer which is insoluble in and impermeable to the fluid medium and impermeable to the diffusible solid. The surfaces of the disc are coated with a polymer which is insoluble in and impermeable to the fluid medium and impermeable to the diffusible solid, and one or more apertures are formed which extend completely through the disc and expose a portion of the mixture of diffusible solid and polymer to the fluid medium when the device is immersed therein. The aperture or apertures are placed in the disc such that as the fluid medium enters the disc through the aperture or apertures, the ratio of surface area of diffusible solid exposed to the fluid medium to the length of the path through which the exposed solid must diffuse to exit the device remains substantially constant. The device may be implanted into body tissues, inserted into a body cavity of a living being or orally ingested by the living being.

The mixture of a diffusible solid and polymer becomes a matrix through which the diffusible solid, a beneficial agent, must diffuse before entering the fluid medium as body fluids gradually penetrate the device from the aperture or apertures. The polymer is substantially insoluble in and impermeable to the fluid medium as well as substantially impermeable to the diffusible solid.

Figure 1:
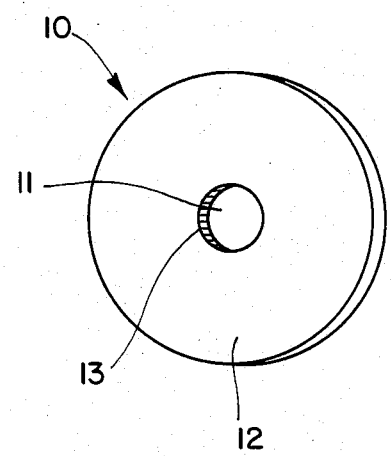
FIG. 1 is the top view of a disc-shaped device of this invention having a centrally located aperture which extends through the device.

FIG. 1 shows the device in its preferred form as a circular disc 10 with one substantially centrally located aperture 11. The disc is completely coated with a polymer 12 except in the aperture where there is an uncoated releasing surface 13. The polymer used for the coating is insoluble in and impermeable to the fluid medium as well as impermeable to the diffusible solid. Applicant has found that the release of the beneficial agent from such a device is substantially zero order or time independent since, as the pathway from where the beneficial agent is located within the device to the aperture or apertures increases as the body fluids penetrate the matrix, the amount of beneficial agent available for release also will increase. The body fluids will penetrate the device through the aperture or apertures and spread radially into the device due to its circular, disc shape. The aperture or apertures are placed in the device such that the ratio of the surface area of diffusible solid exposed to the fluid medium to the length of the path through which the exposed solid must diffuse to exit the disc remains substantially constant. In the preferred embodiment of the invention, the device comprises one aperture which is substantially centrally located. The device may comprise more than one aperture, however. A plurality of apertures may be appropriate, for example, where the diffusible solid is only slightly soluble in the fluid medium and a relatively high rate of release of the solid is sought.

The amount of beneficial agent released will increase steadily with the length of the pathway to the aperture or apertures until the body fluids have completely penetrated the disc and the supply of beneficial agent is depleted, thus making the release of beneficial agent substantially time independent over the entire useful life of the device. The useful life of a device of this invention can vary depending upon various factors, as, for example, the size of the device, the ratio of insoluble polymer to beneficial agent in the matrix, and the size of the aperture or apertures formed in the disc. These factors can be adjusted such that the device can be used over a prolonged period of time, such as 20-30 days.

The diffusible solid to be used in the device of the present invention may be any agent which produces a beneficial effect in the body of living beings. Beneficial effect is defined as a physiologically or pharmacologically useful effect in the body of a living being either at a site in close proximity to the agent's point of release or at a site removed from the release site. Some examples are hypnotics, sedatives, antibiotics, tranquilizers, anticonvulsants, muscle relaxants, anti-bloat agents, antipyretics, anti-inflammatories, analgesics, local anesthetics, muscle contractants, hormones, steroids, anthelmintics, anti-microbials, diuretics, neoplastics, hypoglycemics, amino acids, opthalmic agents, nutritional supplements and vitamins. Other drugs or biologically active proteins are encompassed within the scope of the invention as well.

The polymers used in the matrix with the beneficial agent and as a coating over the device, except on the walls of the aperture or apertures, may be any polymer biocompatible with the body tissues and body fluids of living beings and insoluble in these body fluids. Body fluids include water and aqueous-based fluids such as tissue juices, tear fluids and the like. The polymer to be used in the matrix may be comminuted before mixing with the beneficial agent or the mixture of polymer and beneficial agent may be comminuted before being formed into a disc. The term matrix denotes a carrier polymeric phase comprising a polymer that is biocompatible and sufficiently resistant to chemical and/or physical attack by the environment of use such that the matrix remains intact throughout the prolonged period of time the beneficial agent is released from the device. The polymer matrix suitable for the present invention is biocompatible in the environment of use and is insoluble in and substantially impermeable to the passage of the beneficial agents with which the polymer is mixed. The same polymer which is mixed with a beneficial agent to form the matrix also may be used to coat the entire device with a water insoluble coating, after which an aperture or apertures are formed through the center of the device. The polymer used to coat the disc need not necessarily be the one which was used to form the matrix with the beneficial agent within the disc, but the polymers must be compatible so that the coating polymer will remain attached to the matrix throughout the use of the device. Typical polymeric materials suitable for forming the matrix are the naturally occuring and synthetic commercially available polymers such as acyl substituted cellulose acetates and alkyl derivatives thereof; partially and completely hydrolyzed alkylene-vinyl acetate copolymers; unplasticized polyvinyl chloride; crosslinked homo- and copolymers of polyvinyl acetate; crosslinked polyesters of acrylic and methacrylate; polyvinyl alkyl ethers, polyvinyl fluoride; silicone; polycarbonate; polyurethane; polyamide; polysulphones; styrene acrylonitrate copolymers; crosslinked poly (ethylene oxide); poly(alkylenes); poly(vinyl imidazole); poly(esters); and chlorosulphonated polyolefins. Preferred polymers for use in the matrix are ethylene-vinyl ester copolymers such as ethylene-vinyl acetate, ethylene vinyl methylacetate, ethylene-vinyl ethylacetate and ethylene-vinyl propylacetate. An especially preferred polymer is ethylene-vinyl acetate.

The device of the present invention may be formed from a mixture of about 25 to 75 parts of the beneficial agent and from about 75 to about 25 parts of polymer. Preferably the mixture will contain about 40 to about 60 parts beneficial agent and from about 60 to about 40 parts polymer. The mixture may be compression molded to form the matrix, or it can undergo a solvent coating process. The matrix then is coated with an insoluble polymer and at least one aperture is formed through the coating and the matrix. The diameter of the disc may be about 10 mm to about 15 mm with the aperture or apertures having a diameter between about one-thirteenth and one-third the diameter of the disc or, typically, between 1 and 5 mm. The preferred diameter is between 12 and 13 mm. The preferred diameter of an aperture when the device is in its preferred embodiment wherein there is one substantially centrally located aperture is about one-sixth the diameter of the disc. The thickness of the disc may be between about 1 and 4 mm, preferably between about 1 and 1.5 mm.

The device of this invention is prepared by mixing a polymer which is insoluble in the fluid medium with a diffusible solid, forming a cylindrical disc, coating the disc with the polymer or one compatible with it and making at least one aperture which extends through the disc and the polymeric coating.

To prepare the matrix of polymer and diffusible solid, the beneficial agent may be dispersed in a solution of the polymer and a nonaqueous solvent. After mixing, the solvent is removed under a vacuum and the resulting product comminuted before being compression molded in a pellet press. The discs may be coated by dipping them into a polymer/solvent solution several times or by means of known spraying techniques. After the discs are coated and dried, at least one aperture is formed in each disc, leaving an uncoated surface of the disc through which the beneficial agent can be released.

The device also may be prepared by dispersing the beneficial agent, a diffusible solid, in a solution of a polymer and a nonaqueous solvent, casting the dispersion in a mold and then freezing the molded dispersion. The solvent is removed from the frozen dispersion, leaving a disc which may be coated with a polymer before forming at least one aperture in the disc.

The solvents used in the preparation of the devices of this invention will depend upon the polymer chosen as well as the beneficial agent employed. To prepare a device according to these methods, the polymer must be soluble in the solvent and the beneficial agent must be insoluble in the solvent.

The method chosen for making a disc in accordance with this invention will depend, at least in part, on the nature of the beneficial agent of interest. For example, beneficial agents which are not negatively affected by heat most readily may be mixed with a polymer and compressed. In these situations, heating the mixture eliminates the need for a solvent.

The discs may be implanted in body tissues or inserted into a body cavity of a living being or orally ingested by a living being.

The following example is merely illustrative of the present invention and should not be considered as limiting the scope of the invention.

EXAMPLE 1

Preparation of Ethylene-Vinyl Acetate/Lysozyme Discs

A crude matrix of 50% lysozyme and 50% ethylene vinyl acetate (EVAc) was prepared by mixing 1.7 grams of lysozyme (75 $\mu$ particle size) with 17.0 grams of 10% EVAc in $CH_2Cl_2$. The lysozyme particles were dispersed in the EVAc/$CH_2Cl_2$ solution by vortexing, then the mixture was placed under house vacuum for 18 hours. The resulting mass was ground for 15 seconds in an analytical mill.

150 mg of the EVAc coated lysozyme then was loaded into a Perkin Elmer KBr pellet press, diameter one-half inch. The press was heated to 38°–43° C. and then placed on a Carver press and 15,000 psi were applied for 5 minutes. The resulting discs were placed under house vacuum for 18 hours. The dimensions of the discs are set forth below.

| Pellet Dimensions | |
|---|---|
| Diameter | 12.7 mm |
| Thickness | 1.03 mm |
| Density | 1.085 g/cm$^3$ |

The end of an S-shaped piece of wire then was pushed into the center of each disc. The discs were dipped into a 9% w/w EVAc/$CH_2Cl_2$ solution while holding the top of the wire. The discs were hung out to air dry for two hours after which time they were dipped into the EVAc solution again. They were dipped a total of 4 times, allowed to air dry for 48 hours and then placed under house vacuum for 18 hours.

The wire was removed from each disc and they were placed on the Stokes pelletizing machine which had a 3 millimeter punch and die. A 3 mm hole was made in the center of the disc with the 3 mm punch. The only uncoated surface of the implant is now the releasing surface (indicated by the numeral 13 in FIG. 1) in the center of the device.

The calculations for the order of release of the beneficial agent from the disc prepared as above were performed using the equation $$\text{FRACTION RELEASED} = M_t/M_\infty = Kt^n$$

$M_t$ = quantity of drug released at time t
$M_\infty$ = quantity of drug released at time t = $\infty$ (initial drug loading).

The value of n was determined by plotting the log of time against the log of the fraction of drug released and then fitting a line to this curve. The slope of the line equals n.

The value of n is related to the release as follows:

| Value of n | Type of Drug Release |
|---|---|
| 0.5 | Time dependent $f(t^{-0.5})$ |
| $0.5 < n < 1.0$ | Time dependent $f(t^{n-1})$ |
| 1.0 | Time independent (zero order) |
| $n > 1.0$ | Time dependent $f(t^{n-1})$ |

Figure 2A:
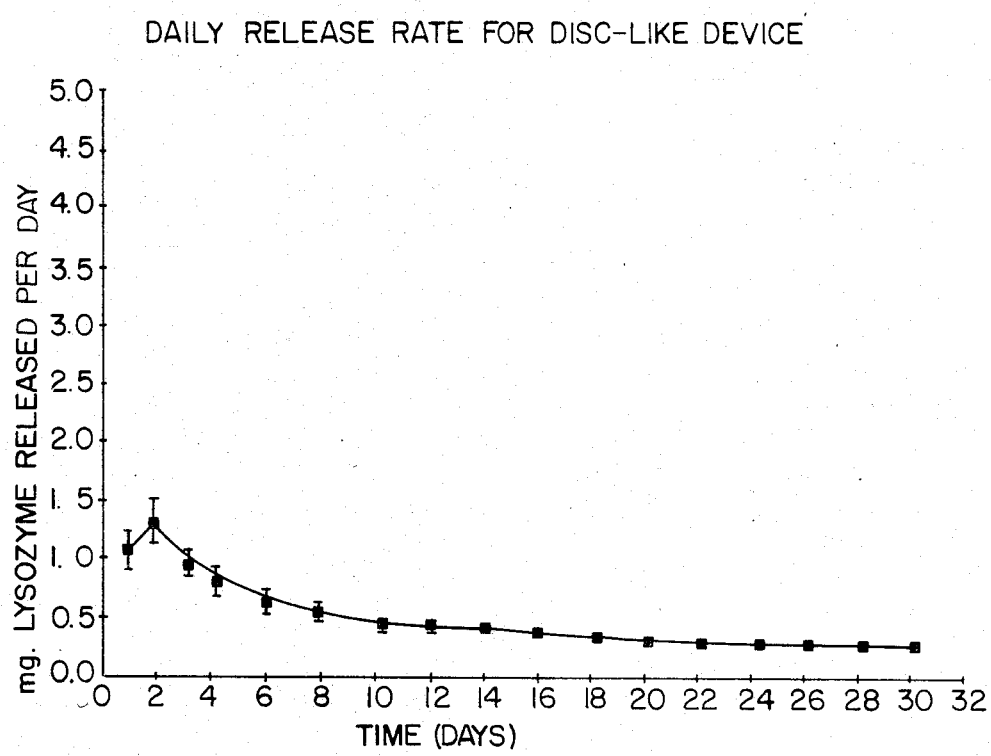
FIG. 2a is a graph which illustates the rate of release of a beneficial agent, lysozyme, from a delivery device of this invention.
Figure 2B:
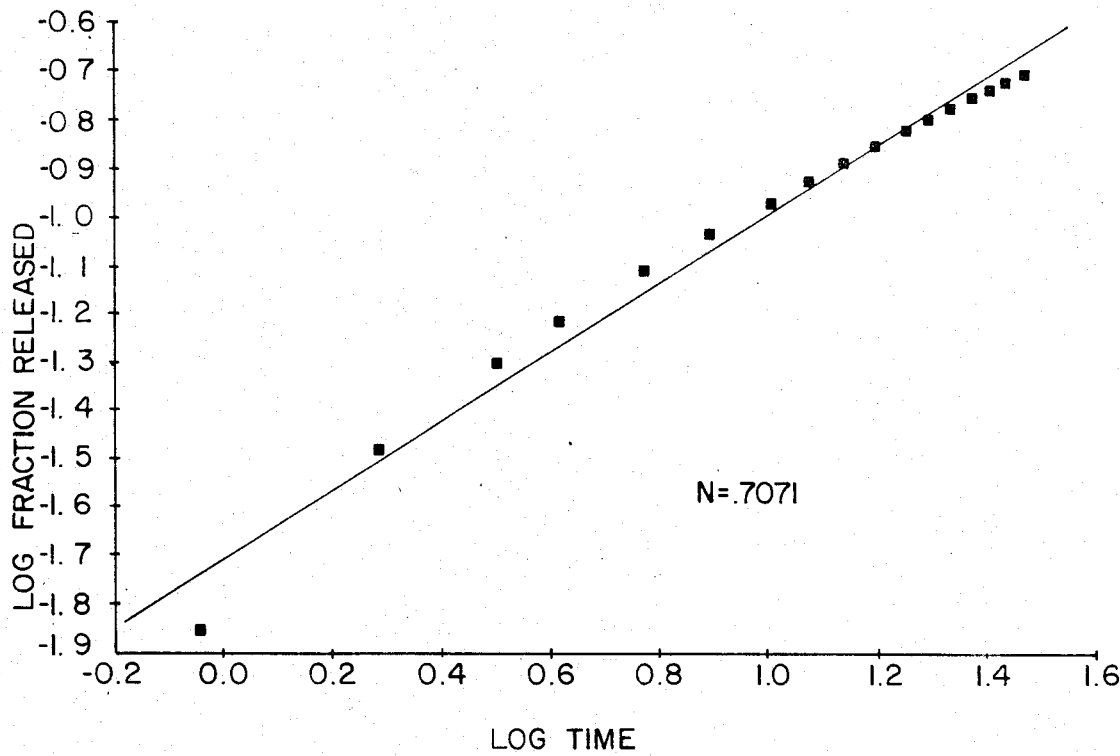
FIG. 2b is a graph which shows the calculation of the n value (see Example I), which is related to the order of release, for the same device of this invention.
Figure 3A:
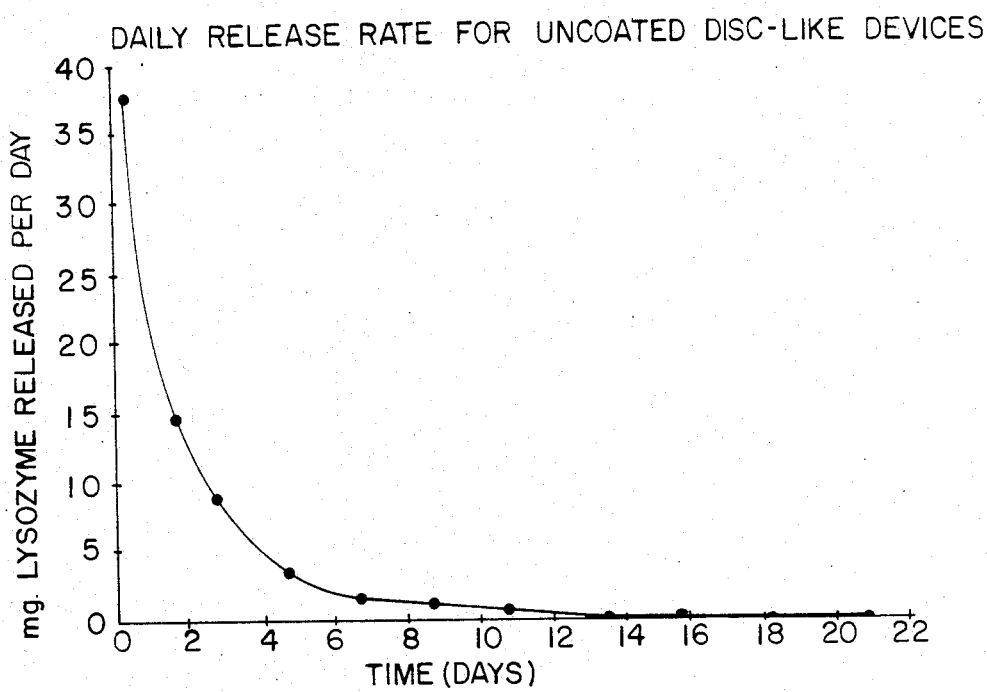
FIG. 3a is a graph which illustrates the rate of release of lysozyme from a conventional delivery device.
Figure 3B:
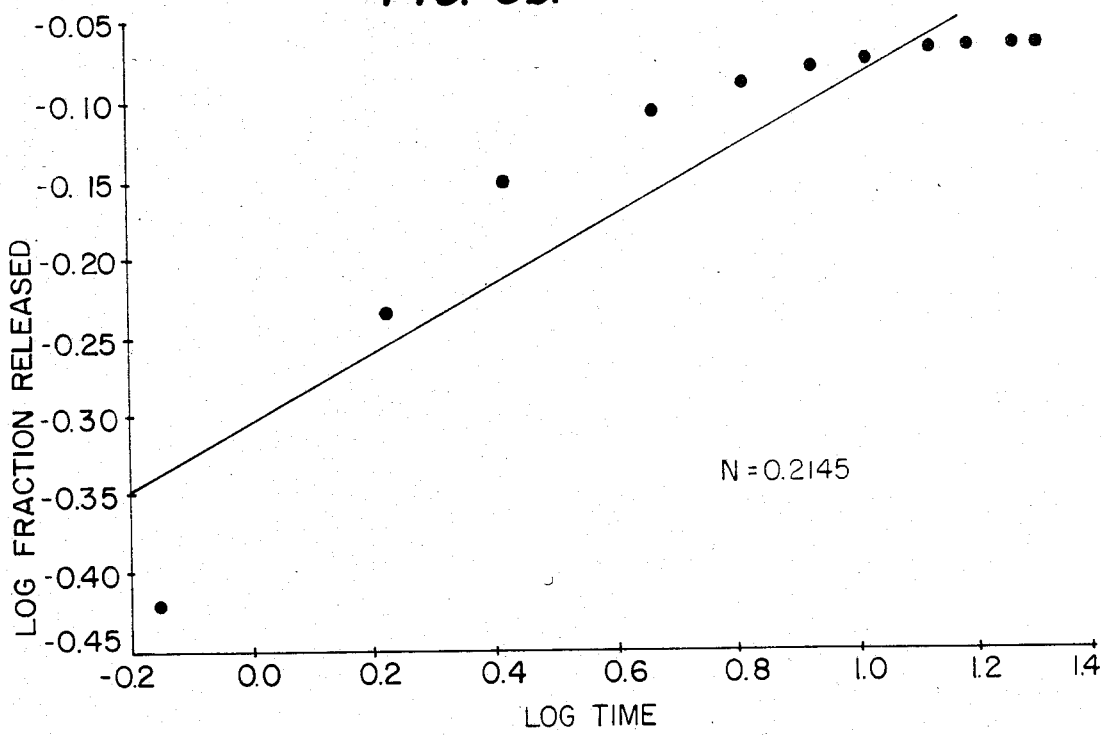
FIG. 3b is a graph which shows the calculation of the n value (see Example I) which is related to the order of release, for the conventional device.

FIGS. 2a and 2b represent the lysozyme release from the disc prepared in this example. The graph of FIG. 2a shows the release rate nearly constnat. The graph of FIG. 2b shows the order of release approaching zero. FIGS. 3a and 3b represent the lysozyme release rate and order from a disc prepared as the disc in this example but lacking a coating of ethylene-vinyl acetate.

What is claimed is:

1. A device for the release of a diffusible solid in a fluid medium which comprises:
    a disc which comprises a substantially uniform mixutre of said diffusible solid and a polymer which is insoluble in and impermeable to said fluid medium and impermeable to said diffusible solid;
    the surfaces of said disc coated with a polymer which is insoluble in and impermeable to said diffusible solid, with the exception that one or more apertures extend through said disc and said polymeric coating and expose a portion of said mixture of diffusible solid and polymer to said fluid medium when said device is immersed therein;
    said aperture or apertures having a total diameter between approximately 1/13 and approximately ⅓ the diameter of the disc; and
    said aperture or apertures so placed in said disc that as said fluid medium enters the disc through said aperture or apertures the ratio of surface area of diffusible solid exposed to said fluid medium to the length of the path through which said exposed solid must diffuse to exit said disc remains substantially constant.

2. A device of claim 1, whrein said diffusible solid is a beneficial agent for living beings and said device can be ingested by, implanted in body tissues of, or inserted into body cavities of said living being.

3. A device of claim 2, wherein the diffusible solid is a physiologically or pharmacologically active substance.

4. The device of claim 1 wherein the polymers are biocompatible with body tissue and body fluids of living beings.

5. The device of claim 1 wherein the polymer mixed with the diffusible solid is the same as the polymer used to coat the surface of the disc.

6. The device of claim 1 which comprises one aperture which is substantially centrally located in said device.

7. The device of claim 1 wherein said insoluble polymers are selected from the group consisting of acyl substituted cellulose acetates and alkyl derivatives thereof; partially and completely hydrolyzed alkylene-vinyl acetate copolymers; unplasticized polyvinyl chloride; crosslinked homo- and copolymers of polyvinyl acetate; crosslinked polyesters of acrylic and methacrylate; polyvinyl alkyl ethers, polyvinyl fluoride; silicone; polycarbonate; polyurethane; polyamide; polysulphones, styrene acrylonitrate copolymers; crosslinked poly(ethylene oxide), poly(alkylenes); poly(vinyl imidazole), poly(esters); and chlorosulphonated polyolefins.

8. The device of claim 7 wherein at least one of said polymers is an ethylene-vinyl ester copolymer.

9. The device of claim 8 wherein at least one of said polymers is ethylene-vinyl acetate.

10. The device of claim 1 which comprises about 25 to about 75 parts of diffusible solid and about 75 to about 25 parts of polymer.

11. The device of claim 10 which comprises about 40 to about 60 parts of diffusible solid and about 60 to about 40 parts of polymer.

12. The device of claim 6 wherein the substantially centrally located aperture has a diameter approximately 1/6 the diameter of the disc.

13. The device of claim 1 wherein the diameter of the disc is about 10 mm to about 15 mm.

14. The device of claim 13 wherein the diameter of the disc is about 12 to about 13 mm.

15. The device of claim 1 wherein the thickness of the disc is about 1 to about 4 mm.

16. THe device of claim 15 whereiin the thickness of the disc is about 1 to about 1.5 mm.

* * * * *